United States Patent [19]

Austin

[11] Patent Number: Plant 7,556

[45] Date of Patent: Jun. 18, 1991

[54] ROSE PLANT — AUSMAN

[75] Inventor: David C. H. Austin, Wolverhampton, England

[73] Assignee: David Austin Roses, Wolverhampton, England

[21] Appl. No.: 435,555

[22] Filed: Nov. 9, 1989

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Ladas & Parry

[57] ABSTRACT

A new variety of rose plant of the shrub class; distinctive in its character by its fully double flowers of greyish—rose with light yellow streaks with abundant continual blooming and the unusual blend of coloring and shaping of the flower.

1 Drawing Sheet

BACKGROUND OF THE INVENTION

The present invention relates to a new and distinct variety of shrub rose, seedling resulting from a definite effort to produce an improvement in this class of roses.

BRIEF SUMMARY OF THE INVENTION

Primary features of this new variety which connote a distinctive advance over existing types are the gross abundant and continual blooming unlike its parent, Comte de Chambord, taken with the perfection of the fully double flowers of an old-fashioned shape, more particularly apparent in the accompanying illustration of a specimen thereof.

BRIEF DESCRIPTION OF THE DRAWING

The drawing is a color photographic representation of a new variety of flush of bloom taken substantially in side view and showing inflorescence in various stages, stems and foliage of the plant.

DETAILED BOTANICAL DESCRIPTION

The following is a detailed description of the new variety, color terminology being in accordance with the "Methuen Handbook of Colour" published by Eyre Methuen Ltd (1963).

Variety denomination (in accordance with the UPOV Convention): Ausman (Trade name The Countryman).

Type: Hardy; bush; seedling; for cut flowers and garden decoration.

Class: shrub.

Propagation: holds its distinguishing characteristics through succeeding propagations by budding.

The rose plant was grown at Albrighton, Nr. Wolverhampton, England as was derived as follows:

Female parent (seed parent): Lilian Austin.

Male parent (pollen parent): Comte de Chambord.

The following observations are made of specimens grown outdoors in England.

PLANT DESCRIPTION

Plant:

*Height.*—110 cm.

*Habit.*—Dense and bushy.

Branches:

*Young stems.*—Color: 29D7 Greyish green widely shaded with a reddish tint 9D8. Texture: Smooth, dull. Thorns: Many, various sizes, downward pointing, all but the largest with glandular ends. Reddish brown color 9E6 fading to champagne 4B4 at tips (and base of very mature thorns).

*Old stems.*—Color: 29D6 Greyish green. Texture: Dull. Thorns: Many, various sizes (1–6 mm) downward pointing. All but the largest with glandular ends. Reddish brown 9E6 fading to cream 4A3 underneath.

Leaves:

*Stipules.*—Length: av. 23 mm. Width: 3–5 mm. Color of mid line: Raspberry 10D7 in young wood turning to yellowish white 3A2 in mature wood. Angle of wingtips to petiole: less than 45° wingtips moderately long 3–5 mm. Margins: Densely lined with red glandular hairs. Underside dotted sparsely with red glandular hair. Upperside glabrous.

Petiole:

*General description.*—Slender. Length: 70 mm.

*Upperside color.*—Young wood deeply tinted with raspberry red 10D7 fading in old wood to 29D7 greyish green.

*Groove/hairs/thorns.*—Red glandular hairs on margin of groove.

*Underside color.*—Greyish yellow 1B6/greyish green 1C6 mature wood, tinged with red 10D7 in young wood.

*Hair/thorns.*—Sparse downwardly curved thorns. Young leaves thorns are reddish 10D7, in mature woods thorns are yellowish white 1A2.

*Leaflets.*—Number: 3 or 5 most often. Shape: Oval with rounded base obtuse apex. Serration: Dentate with sparse glandular hairs on very young leaves. Texture: Dull, leathery.

General effect of foliage: Dull, medium dense.

Colour:

*Very young foliage.*—Upperside: Olive 1E8 with reddish tinge, more pronounced at margins. Underside: Greyish green 29D6 with reddish tinge, more pronounced at margins.

Adult foliage.—Upperside: 29F6 dark green. Underside: 29E6 spinach green. Margins: Red in immature wood, this disappears in mature wood.

INFLORESCENCE

Number of flowers per stem: 3-7 occasionally 1 or 2.

Peduncle:

*Length.*—15-35 mm most often about 30 mm. First flower shorter.

Thorns/hairs: Straight flexible.

Color: 30D7 lettuce green (greyish) in young wood deepening to deep green 29D8 in mature buds. More or less shades with a reddish tinge, this more pronounced in young buds.

Sepals:

*Upperside color.*—Greyish green 29D7.

*Outer margins.*—Glabrous. Ensiform protrusions with glandular hairs.

*Inner margins.*—Tomentose with fine white downy hairs.

*Apex.*—Drawn out into a lanceolate appendage with glandular margins.

*Underside color.*—Greyish green 29D6 fading at base to 30A4 pastel green.

*Underside texture.*—Densely tomentose.

*Sepal length.*—25-30 mm when finished flowering.

*Bud shape.*—Oval with cuspidate apex. Length: 25-30 mm average (before bud break).

*Max. width.*—10-12 mm.

*Color when opening.*—Deep red 11C8 at top changing through light yellow 4A4 to yellow 3A5 at base.

*Flower shape.*—As a flattened cap. Outer petals recurved towards stem, inner petals inwardly curved.

*Diameter.*—Typically 60-80 mm.

*Flower color when opening.*—Upperside: Greyish rose 12B6 some patches of yellow 3A7 toward center. Underside: Greyish ruby 12C4 yellowing through pale orange 5A3 to light yellow 3A5 at base.

*Flower color when blooming.*—Upperside: Greyish rose 12B5 with light yellow 4A4 streaks which occur in all petals and are always along the midpoint of the petal. Midline: Base of petal yellow 3A5. Underside: Greyish rose 12B4 yellowing to pale yellow 4A3 at base.

*Flower coloring when finished blooming.*—Upperside: 12A3 pale red with pale yellow 4A3 center. Underside: Greyish ruby 12C3 paling to yellowing white 4A2 at base.

*Length of blooming season in location of production.*—end of June to beginning of October.

Fragrance: Very good old rose fragrance.

Lasting quality: Very good will stay on the plant for 13-16 days and cut flowers will last 8-10 days.

Petals:

*Shape outside.*—Rounded with roughly bilobed top and cuneate base. Inside: Narrower, still bilobed with retuse apex and pointed base.

*Texture.*—Medium to leathery.

*Number.*—100-110, inner ±10 exhibit staminody to varying degrees.

*Cleaning.*—Very good.

Stamens:

*Number.*—100-110.

*Anthers.*—Normal, bright yellow 3A8.

*Filaments.*—Yellow 3A6, of irregular heights.

Pistils:

*Number.*—More than 110, numerous.

*Stigmas.*—Central stigmas, normal strawcolored 3B4. Outer stigmas: fuschure 13A8 streaks.

*Styles.*—Central: Greenish yellow 1A8 tomentose, irregular height. Outer: fuschure 13A8 streaks near apex.

Receptacle:

*Color.*—29D7 Greyish green. Young receptacles have red 9C8, glandular hairs mostly absent at dehiscence.

*Size.*—Jug-shaped in longitudinal section.

*Length.*—12-15 mm×width 8-10 mm.

The development: Vegatation; vigorous.

Blooming: Abundant and continual.

Aptitude to bear fruits: None.

Resistance to frost: Good.

Resistance to diseases: Good.

I claim:

1. A new and distinct variety of rose plant of the shrub class, characterized as to novelty by its fully double flowers, of greyish—rose with light yellow streaks with abundant and continual blooming and the unusual blend of coloring and shaping of the flower being substantially as shown and described.

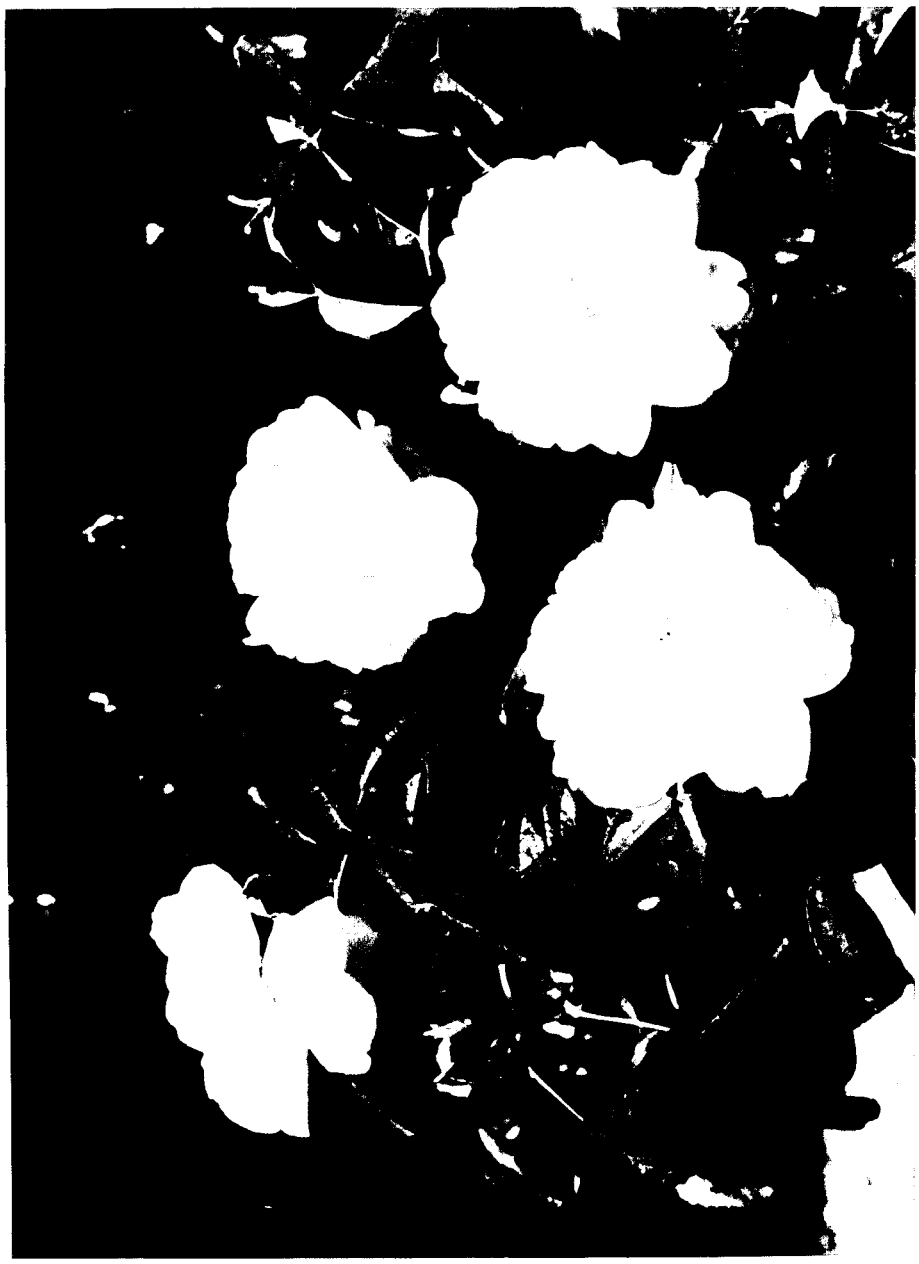

* * * * *